Figure 1:
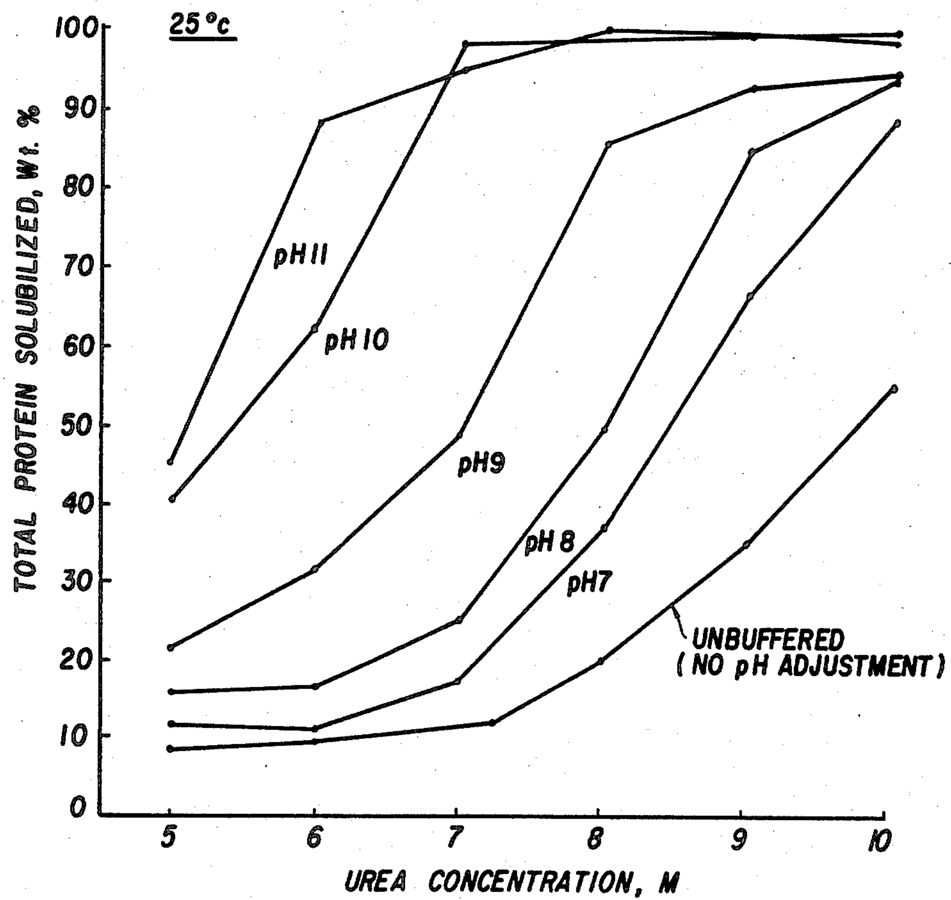

United States Patent [19]

Bentle et al.

[11] Patent Number: 4,694,073

[45] Date of Patent: Sep. 15, 1987

[54] METHOD OF SOMATOTROPIN SOLUBILIZATION AND NATURATION USING DIMETHYLSULFOXIDE

[75] Inventors: Larry A. Bentle, St. Charles; James W. Mitchell, St. Louis; Stephen B. Storrs, Creve Coeur; Grant T. Shimamoto, Maryland Heights, all of Mo.

[73] Assignee: Monsanto Company, St. Louis, Mo.

[21] Appl. No.: 900,017

[22] Filed: Aug. 25, 1986

Related U.S. Application Data

[63] Continuation-in-part of Ser. No. 704,341, Feb. 22, 1985, and a continuation-in-part of Ser. No. 704,677, Feb. 22, 1985, Pat. No. 4,652,630.

[30] Foreign Application Priority Data

Feb. 20, 1986 [ES] Spain ..................................... 552233

[51] Int. Cl.[4] ......................... C07K 15/00; C07K 3/08

[52] U.S. Cl. .................................... 530/399; 424/108; 514/2; 514/21; 530/397; 530/410; 530/808; 530/825

[58] Field of Search ............... 530/395, 397, 399, 410, 530/825, 808

[56] References Cited

U.S. PATENT DOCUMENTS 4,342,832 8/1982 Goeddel et al. .................. 435/68 X
4,512,922 4/1985 Jones et al. ..................... 530/399 X

FOREIGN PATENT DOCUMENTS 0075444 3/1983 European Pat. Off. .
0111389 6/1984 European Pat. Off. .

OTHER PUBLICATIONS

Archives of Biochemistry & Biophysics, 138 (1970), 338–346, Bewley et al.
Methods in Enzymology, XXXIV, 67, 544–547 (1974), Sluyterman et al.
FEBS Letters, 80, No. 2, 408–412 (1977), Kohl et al.
Biochemistry, 2nd ed. (1981), Stryer, pp. 32–35.

*Primary Examiner*—Howard E. Schain
*Attorney, Agent, or Firm*—Jon H. Beusen; George R. Beck; Howard C. Stanley

[57] ABSTRACT

A method for solubilization and naturation of somatotropin protein from refractile bodies of host cells is disclosed. The method embraces the discovery that an aqueous solution of urea, or dimethylsulfone, or mixtures of urea and dimethylsulfone, can be effectively used to solubilize refractile bodies containing such somatotropin protein. Once solubilized, somatotropin protein can be natured in an aqueous solution of urea, or dimethylsulfone, or mixtures of urea and dimethylsulfone, by contacting the solution with a mild oxidizing agent for a time sufficient to result in the formation of the disulfide bonds. Naturation can efficiently occur even at high protein concentration, in an impure preparation and in the absence of reducing agent.

19 Claims, 5 Drawing Figures

METHOD OF SOMATOTROPIN SOLUBILIZATION AND NATURATION USING DIMETHYLSULFOXIDE

This application is a continuation-in-part of applications Ser. No. 704,341 filed Feb. 22, 1985 and Ser. No. 704,677, filed Feb. 22, 1985, now U.S. Pat. No. 4,652,630.

Recombinant DNA technology has permitted the expression of heterologous protein in host cells such as *E. coli* bacteria. It has been reported that some heterologous proteins such as the somatotropins (growth hormones) are sequestered, in varying extent following expression, in refractile bodies within the cytoplasm of the host cell.

Chaotropic agents such as guanidine hydrochloride, sodium thiocyanate, urea and various detergents have been used to disrupt the non-covalent intermolecular attractions within proteins. For example, it has been shown that proteins can be "unfolded" by exposing the protein to a chaotropic agent, see Stryer, Biochemistry (2nd edition, 1981) pp 34–35, W. H. Freeman and Company. Likewise, it has been shown that proteins which contain multiple subunits can be dissociated into their respective subunits by exposing the protein to a chaotropic agent.

It has been recently reported in European Patent Application publication number 114,506A that heterologous proteins can be solubilized from refractile bodies using a strong chaotropic agent such as guanidine hydrochloride, detergents such as sodium dodecyl sulfate and salts of thiocyanate. The use of urea, a relatively weak chaotropic agent, to solubilize refractile bodies was reported to be ineffective. Strong denaturants such as guanidine hydrochloride are quite expensive. Moreover, once solubilized in the strong denaturant the heterologous protein must be exchanged into a weak denaturant that will not interfere with downstream ion exchange purification procedures.

Other solvents have been used for solubilization and extraction of proteins. For example, in the publication of Brigette Kohl et al ["Solubilization of *Escherichia coli* Membrane Proteins by Aprotic Solvents", *FEBS Letters,* Vol. 80, No. 2, 408–412 (August, 1977)], there is described the use of dimethylsulfoxide (DMSO) as a solvent for extracting proteins from *E. coli* cell membranes, such proteins having molecular weights in a range from about 25,000 to about 68,000 Daltons. Also, dimethylsulfoxide has been used to improve solubility of proteins for column chromatographic separations, such proteins being bovine hemoglobin, chymopapain, and streptococcal proteinase [L. A. Ae. Sluyterman et al, "Organomercurial Agarose", *Methods in Enzymology,* XXXIV, 67, 544–547 (1974)].

The effect on protein denaturation by mixtures of urea with other solvents has been reported. For example, enhancement of the denaturation effect of urea on a solution of bovine serum albumin by the presence of DMSO in the urea solution has been described [L. D'Ambrosio el al, "Electrophoretic Study On Urea-denatured Serum Proteins In Aqueous Media Containing Dimethyl Sulfoxide", *Rend. Atti Accad. Med. Chir.,* Vol. 127, 52–60 (1973)]. In another study, a mixture of urea and DMSO provided a denaturing medium for bovine β-lactoglobulin [C. N. Pace et al, "A Comparison of the Effectiveness of Protein Denaturants for β-Lactoglobulin and Ribonuclease", *Arch. Biochem. Biophys.,* Vol. 199, No. 1, 270–276 (1980)].

Accordingly, it is an object of the present invention to provide improved methods for solubilization and subsequent naturation of heterologous somatotropin proteins from refractile bodies of host cells.

It is an object of the present invention to provide methods which use a readily available and relatively inexpensive agent.

It is another object of the present invention to provide a method in which the naturation step can be conducted at a relatively high somatotropin concentration.

It is yet another object of the present invention to provide such methods wherein solubilization and/or naturation of somatotropin proteins can be carried out in the presence or absence of reducing agent.

It is still another object of the present invention to provide such methods which use an agent that is ecologically safer than agents used in prior methods.

These and other objects and advantages of the present invention will be evident to those skilled in the art from the following description and examples.

DESCRIPTION OF THE INVENTION

Briefly, the present invention provides methods of solubilization and subsequent naturation of somatotropin protein from refractile bodies of host cells. More particularly, the present method embraces the discovery that an aqueous solution of urea, or dimethylsulfone, or mixtures thereof, can be effectively used to solubilize refractile bodies containing such somatotropin protein. Surprisingly, it has been further found that once solubilized, such somatotropin protein can be natured in an aqueous solution of urea, or dimethylsulfone, or mixtures thereof, by contacting the solution with a mild oxidizing agent for a time sufficient to result in the formation of the disulfide bonds present in the native conformation of the protein. Naturation can efficiently occur even at high protein concentration, in an impure preparation and in the absence of reducing agent.

For purposes of the present invention, the following terms should be considered to have the definitions listed below.

The term "somatotropin" is meant to include, but not limited to, mammalian somatotropins, such as human, ovine, porcine and bovine somatotropin, and others such as avian somatotropin. In addition to being suitable for the above somatotropin proteins having naturally occurring sequences, the present invention is equally applicable to systems involving analogs and homologs of the naturally occurring protein having somatotropin-like bioactivity. It will be understood by those skilled in the art that other somatotropinlike proteins having similar chemical properties such as prolactin and placental lactogen are considered for purification purposes substantially equivalent to somatotropins. Accordingly, to the extent that such proteins are equivalents for purification purposes the present invention includes such proteins.

"Heterologous" proteins are proteins which are normally not produced by the host cell. Recombinant DNA technology has permitted the expression of relatively large amounts of heterologous proteins from transformed host cells. However, while not fully understood, these foreign proteins are often sequestered in insoluble light refractile bodies in the cytoplasm of the host cell.

By "refractile bodies" is meant the inclusion bodies or cytoplasmic aggregates containing, at least in part, the heterologous somatotropin to be recovered. These aggregates appear as bright spots under a phase contrast microscope.

By "host cell" is meant a microbial cell such as bacteria and yeast or other suitable cells such as animal and plant cells which has been transformed to express the heterologous somatotropin. Host cells which are contemplated by the present invention are those in which the heterologous somatotropin is sequestered following expression in refractile bodies. An exemplary host cell is *E. coli* K12 (strain W3110/pBGH-1) which has been transformed to permit expression of bovine somatotropin.

"Naturation" refers to the folding and oxidation of the somatotropin protein to its native conformation to ensure biological activity.

"Folding" refers to the return of the overall conformational shape of the protein sufficient to permit proper oxidation. Folding is accomplished by reducing the denaturing effect of the urea by adjusting the urea concentration to a suitable level, if necessary, to permit the amino acids sequence of the protein to interact and assume its native secondary and tertiary structure.

"Oxidation" refers to the formation of the intramolecular disulfide bonds to obtain the stable native conformation to ensure biological activity.

By "mild oxidizing agent" is meant an agent which promotes the oxidtion of the sulfhydral groups thereby forming the intramolecular disulfide bonds while not oxidizing other substituent groups of the subject protein. While mild agents such as hydrogen peroxide may be used, exposure to air is quite acceptable and is preferred.

By "biological activity" is meant that the somatotropin is capable of effecting its intended in vivo physiological response. The biological activity can be determined in the absence of in vivo testing in the particular species by carrying out suitable bioassays. A suitable bioassay for the somatotropins embraced by this invention is the "rat weight gain bioassay". In this bioassay the bioactivity of somatotropin preparations are assessed relative to a known preparation (i.e. extracted native somatotropin) by relating the amount of weight gain of hypophysectomized rats to varying amounts of administered preparation.

Somatotropins are hormones which are secreted by the adenohypophysis (anterior lobe of the pituitary gland) and are known to effect the rate of skeletal growth and gain in body weight. Administration of somatotropin has been shown to cause an increase in milk production in lactating animals such as dairy cows and goats. Typically, somatotropins contain approximately 191 amino acid residues and have an approximate molecular weight of 22,000 daltons. The complete amino acid sequences have been established for somatotropins from several species, including humans and animals such as birds (avian), sheep (ovine), pig (porcine) and cattle (bovine). A comparison of the amino acid sequence from the species listed above indicates a relatively high overall homology when considering "conservative" amino acid replacements. In general terms, some "conservative" substitutions can occur without substantial change in the gross chemical properties of a protein. Exemplary of such substitution are substitution of aliphatic hydrophobic residues for one another (isoleucine, valine, leucine and methionine) and substitution of polar residues for one another (arginine for lysine, glutamine for asparagine and glutamic acid for aspartic acid). Ionic residues of opposite charge have been shown to substitute for one another, for example, aspartic acid or glutamic acid for lysine. Moreover, substitutions that are "radical" (representing different kinds of side chains) can occur without substantial change in function or chemical properties when the locus of substitution is not critical for conformation and the degree of substitution is not extensive.

In Table I below is shown the reported primary configuration for somatotropins of various animal species. The following abbreviations are used in Table I: BGH (bovine somatotropin); PGH (porcine somatotropin, i.e., pig); OGH (ovine somatotropin, i.e., sheep); AGH (avian somatotropin, i.e., poultry); HGH (human somatotropin). The symbol "X" denotes a space in the sequence, inserted only to demonstrate the alignment of the representative somatotropins. Numbering in a particular sequence would eliminate this insertion. For example, in BGH position 126 is Leu (or Val as in the allelic variation used in Example 10).

TABLE I

Amino Acid Sequences for Representative Somatotropins

| | 1 | | | | | | | | | 10 | | | | | | | | | | 20 |
|---|---|---|---|---|---|---|---|---|---|---|---|---|---|---|---|---|---|---|---|---|
| BGH | Phe | Pro | Ala | Met | Ser | Leu | Ser | Gly | Leu | Phe | Ala | Asn | Ala | Val | Leu | Arg | Ala | Gln | His | Leu |
| PGH | — | — | — | — | Pro | — | — | Ser | — | — | — | — | — | — | — | — | — | — | — | — |
| OGH | — | — | — | — | — | — | — | — | — | — | — | — | — | — | — | — | — | — | — | — |
| AGH | — | — | — | — | Pro | — | — | Asn | — | — | — | — | — | — | — | — | — | — | — | — |
| HGH | — | — | Thr | Ile | Pro | — | — | Arg | — | — | Asp | — | — | Met | — | — | — | His | Arg | — |

| | | | | | | | | | | 30 | | | | | | | | | | 40 |
|---|---|---|---|---|---|---|---|---|---|---|---|---|---|---|---|---|---|---|---|---|
| BGH | His | Gln | Leu | Ala | Ala | Asp | Thr | Phe | Lys | Glu | Phe | Glu | Arg | Thr | Tyr | Ile | Pro | Glu | Gly | Gln |
| PGH | — | — | — | — | — | — | — | Tyr | — | — | — | — | — | Ala | — | — | — | — | — | — |
| OGH | — | — | — | — | — | — | — | — | — | — | — | — | — | — | — | — | — | — | — | — |
| AGH | — | Leu | — | — | — | Gln | — | Tyr | — | — | — | — | — | — | — | — | — | — | Asp | — |
| HGH | — | — | — | — | Phe | — | — | Tyr | Gln | — | — | — | Glu | Ala | — | — | — | Lys | Glu | — |

```
                                          50                                        60
BGH  Arg—Try—Ser—X— —Ile—Gln—Asn—Thr—Gln—Val—Ala—Phe—Cys—Phe—Ser—Glu—Thr—Ile—Pro—Ala—
PGH  — — — — — — — — — — — — — — Ala— — — Ala— — — — — — — — — — — — — — — — — — — — —
OGH  — — — — — — — — — — — — — — — — — — — — — — — — — — — — — — — — — — — — — — — —
AGH  — — — — Thr— — — Asn—Lys — — Ser— — — Val— — — — — — — Tyr— — — — — — — — — — — —
HGH  Lys— — — — — — Phe—Leu — — — — Pro— — — Thr—Ser—Leu — — — — — — — — — — Ser— — — —Thr—

                                          70                                        80
BGH  Pro—Thr—Gly—Lys—Asp—Glu—Ala—Gln—Gln—Lys—Ser—Asp—Leu—Glu—Leu —Leu—Arg—Ile—Ser—Leu —
PGH  — — — — — — — — — — — — — — — — — — — Arg— — — — Val — — — — — — — — — — Phe — — — —
OGH  — — — — — — — — — — — — — — — — — — — — — — — — — — — — — — — — — — — — — — — — —
AGH  — — — — — — — — Asp—Asp— — — — — — — — — — — — — — Met—Gly— — — — — — — Phe — — — —
HGH  — — Ser—Asn—Arg—Glu— — — Thr— — — — — — — — — —Asn— — — Gln— — — — — — — — — — — — — —

                                          90                                        100
BGH  Leu—Leu—Ile—Gln—Ser—Trp—Leu—Gly—Pro—Leu—Gln—Phe—Leu—Ser—Arg—Val—Phe—Thr—Asn—Ser—
PGH  — — — — — — — — — — — — — — — — — — — — — — — — — — — — — — — — — — — — — — — —
OGH  — — — — — — — — — — — — — — — — — — — — — — — — — — — — — — — — — — — — — — — —
AGH  Val— — — — — — — — — — — — — — Thr— — — Val— — — Tyr— — — — — — Lys— — — — — — — — — Asn—
HGH  — — — — — — — — — — — — — — — Glu— — — Val— — — — — — — — Arg—Ser— — — — —Ala— — — — —

                                          110                                       120
     Leu—Val—Phe—Gly—Thr—Ser—Asp—Arg—X— —Val—Tyr—Glu—Lys—Leu—Lys—Asp—Leu—Glu—Glu—Gly—
BGH  — — — — — — — — — — — — — — — — — — — — — — — — — — — — — — — — — — — — — — — — —
PGH  — — — — — — — — — — — — — — — — — — — — — — — — — — — — — — — — — — — — — — — — —
OGH  — — — — — — — — — — — — — — — — — — — — Phe— — — — — — — — — — — — — — — — — — — —
AGH  — — — — Try— — — Ala— — — Asn—Ser— Asp — — — — — Asp—Leu — — — — — — — — — — — — — — —
HGH                                       130                                       140
     Ile —Leu—Ala—Leu—Met—Arg—Glu—Leu—Glu—Asp—Gly—Thr—Pro—Arg—Ala—Gly—Gln—Ile—Leu—Lys—
     — — Gln— — — — — — — — — — — — — — — — — — — — Ser— — — — — — — — — — — — — — — — —
     — — — — — — — — — — — — — — — — — — — — Val— — — — — — — — — — — — — — — — — — — —
     — — Gln — — — — — — — — — — — — — — — — — — Arg—Ser — — — — — Gly—Pro— — — Leu — — Arg—
     — — Gln—Thr — — — — Gly—Arg— — — — — — — — — Ser — — — — Thr— — — — — —Phe — — —

                                          150                                       160
BGH  Gln—Thr—Tyr—Asp—Lys—Phe—Asp—Thr—Asn—Met—Arg—Ser—Asp—Asp—Ala—Leu—Leu—Lys—Asn—Tyr—
PGH  — — — — — — — — — — — — — — — — — — — Leu— — — — — — — — — — — — — — — — — — — — —
OGH  — — — — — — — — — — — — — — — — — — — — — — — — — — — — — — — — — — — — — — — — —
AGH  Pro— — — — — — — — — — — — — — — — Ile —His—Leu— — — Asn—Glu — — — — — — — — — — — — — —
HGH  — — — — — — — Ser— — — — — — — — — — — — Ser— His—Asn— — — — — — — — — — — — — — — — —

                                          170                                       180
BGH  Gly—Leu—Leu—Ser—Cys—Phe—Arg—Lys—Asp—Leu—His—Lys—Thr—Glu—Thr—Tyr—Leu—Arg—Val—Met—
PGH  — — — — — — — — — — — — — Lys— — — — — — — — — — — — —Ala— — — — — — — — — — — — — — — —
OGH  — — — — — — — — — — — — — — — — — — — — — — — — — — — — — — — — — — — — — — — — —
AGH  — — — — — — — — — — — — —Lys— — — — — — — — — — — —Val— — — — — — — — — — Lys — — — —
HGH  — — — — — — —Tyr— — — — — — — — — — — —Met—Asp— — —Val — — — — Phe— — — — — — Ile —Val —

                                          190
BGH  Lys—Cys—Arg—Arg—Phe—Gly—Glu—Ala—Ser—Cys—Ala—Phe—
PGH  — — — — — — — — — — — — Val— — — Ser— — — — — — — — — —
OGH  — — — — — — — — — — — — — — — — — — — — — — — — — — — —
AGH  — — — — — — — — — — — — — — — — — — Ser—Asn— — —Thr—Ile —
HGH  Gln— — —X— — — —Ser— Val— — — Gly— — — — — —Gly— — —
```

A tabulation of the relative amounts of particular amino acids, based on the reported sequences, is provided below in Table II.

TABLE II

Amino Acid Composition of Representative Somatotropins

| Amino Acid | Human | Bovine | Ovine | Porcine | Avian |
|---|---|---|---|---|---|
| Aspartic Acid | 11 | 10 | 10 | 10 | 11 |
| Asparagine | 9 | 6 | 6 | 5 | 9 |
| Threonine | 10 | 12 | 2 | 8 | 11 |
| Serine | 18 | 13 | 13 | 15 | 11 |
| Glutamic Acid | 14 | 13 | 13 | 13 | 12 |
| Glutamic | 13 | 11 | 11 | 12 | 10 |

TABLE II-continued

Amino Acid Composition of Representative Somatotropins

| Amino Acid | Human | Bovine | Ovine | Porcine | Avian |
|---|---|---|---|---|---|
| Proline | 8 | 6 | 6 | 7 | 9 |
| Glycine | 8 | 10 | 9 | 8 | 7 |
| alanine | 7 | 14 | 14 | 17 | 12 |
| Valine | 7 | 6 | 7 | 7 | 8 |
| Methionine | 3 | 4 | 4 | 3 | 4 |
| Isoleucine | 8 | 7 | 7 | 6 | 6 |
| Leucine | 26 | 27 | 27 | 26 | 26 |
| Tyrosine | 8 | 6 | 6 | 7 | 8 |
| Phenylalanine | 13 | 13 | 13 | 13 | 11 |
| Histadine | 3 | 3 | 3 | 3 | 4 |

TABLE II-continued

Amino Acid Composition of Representative Somatotropins

| Amino Acid | Human | Bovine | Ovine | Porcine | Avian |
|---|---|---|---|---|---|
| Lysine | 9 | 11 | 11 | 11 | 14 |
| Arginine | 11 | 13 | 13 | 12 | 12 |
| Trytophan | 1 | 1 | 1 | 1 | 1 |
| Cysteine | 4 | 4 | 4 | 4 | 4 |

Disulfide bridges in somatotropin proteins are reported to be homogeneously two in number. It is now well supported in the literature that mammalian somatotropins form a relatively homogeneous family of proteins.

It has been reported that most heterologous proteins expressed in *E. coli* bacteria are sequestered, in varied extent following expression, in refractile bodies within the cytoplasm of the bacteria. While not fully understood, this is believed to result, at least in part, from the overproduction of the heterologous protein in the host cell. Heterologous somatotropins are believed to be present in the refractile bodies in substantially reduced form (without disufide linkages) due to the relatively high redox potential of the *E. coli* cell.

Numerous somatotropins have been expressed in *E. coli* bacteria. For example, human somatotropin (*E coli* K12 strain W3110/p107) as disclosed in U.S. Pat. No. 4,342,832; bovine somatotropin (*E. coli* K12 strain W3110/pBGH-1) as disclosed in European Patent Application Publication No. 75,444A (U.S. appln. Ser. No. 303,687, filed 9/18/81); porcine somatotropin as disclosed in European Patent application Publication No. 111,389A (U.S. appln. Ser. No. 439,977, filed 11/8/1982); and avian somatotropin as disclosed in PCT Application Publication No. W084/01150 filed Sept. 13, 1983.

For purposes of the present invention, refractile bodies can be recovered using standard biological techniques. For example, the host cell, previously killed with a solution 0.25 weight percent in both toluene and phenol can be disrupted by commonly used mechanical means such as a Manton-Gaulin homogenizer or French press. It is preferred that the disruption process is conducted such that cellular debris from the host organism is sufficiently disrupted such that it fails to sediment from the homogenate solution under low speed centrifugation. Under low speed centrifugation, the refractile bodies sediment from the homogenate solution. The refractile bodies are preferably resuspended, washed and centrifuged again. The supernatant is discarded yielding a substantially pure preparation. Although not critical to the practice of the present invention, it is preferred that the refractile body preparation be homogenized again to ensure a freely dispersed preparation devoid of agglomerated refractile bodies. The preparation is preferably homogenized in a Manton-Gaulin homogenizer at 3000–5000 psig.

While it has been previously reported that urea is an effective agent to unfold proteins and dissociate multiunit protein into their respective subunits, it has now been found, contrary to prior teachings, that somatotropins can be efficiently solubilized from refractile bodies of the host cell by subjecting the refractile bodies to an effective amount and concentration of urea. It will be evident from the discussion below that urea is an effective solubilization agent at particular concentrations and pH. Alternately, alkaline dimethylsulfone in water has been found to be an effective solvent system to solubilize somatotropins from refractile bodies. While it is anticipated that in most cases urea or dimethylsulfone will be used alone, in some cases one may choose to use these agents in combination with one another.

The concentration and absolute amount of urea, or dimethylsulfone, or mixtures of urea and dimethylsulfone needed will depend on the pH, the particular somatotropin, and amount of protein to be solubilized. The use of urea, or dimethylsulfone, or mixtures thereof, is economically favored since they are readily available, relatively inexpensive, ecologically safer than stronger chaotropic agents and do not substantially interfere with the downstream purification procedures.

For clarity and brevity of explanation, the following description is provided with emphasis on the use of urea. However, those skilled in the art will recognize that the same type process parameters (e.g. concentration, absolute amount, pH, temperature, etc.) will affect the results obtained with dimethylsulfone (see Example 13), or with urea-dimethylsulfone (see Example 14). As used herein, the phrase "urea-dimethylsulfone" means a mixture of urea and dimethylsulfone in any ratio.

Refractile bodies of *E. coli* containing somatotropin proteins were solubilized in varying extent in an aqueous solution containing between about 8M and 10M urea at near neutral pH. Only partial solubilization of relatively small quantities of an essentially pure refractile body preparation is obtained with urea at near neutral pH within a short time. As the urea concentration is decreased the extent of solubilization decreases. At a urea concentration much below about 8M and near neutral pH little solubilization can be detected.

Hydrophobic proteins are, in general, more soluble in aqueous solution at reduced temperatures. With respect to the present invention, it was found that solubilization of the somatotropin-like proteins by urea was greater at reduced temperatures, typically 4° C., than at room temperatures, typically 20° C.–25° C. In addition to greater solubility, solubilization at reduced temperatures results in increased stability of the urea solution and inhibition of protease activity which may be present in the refractile body preparation. While the advantageous effects described above have been shown to result from operating at reduced temperatures, such operation is not critical to the present invention. Rather, one may choose other temperatures as long as the protein is not irreversibly denatured. However, in most cases it is expected that temperatures below 25° C. but above the freezing point of the solution will be most advantageous and are therefore preferred.

In the present invention solubilization of significant quantities of somatotropin protein was attained by increasing or decreasing the pH of the aqueous urea solution. While the unexpected effect of adjusting the solution pH to a more acidic or alkaline pH will be evident from the following examples, adjustment to an alkaline pH is preferred since the naturation step, specifically the oxidation of the reduced monomer, is base catalyzed. The pH of the solution may be made more alkaline by addition of a suitable base such as sodium hydroxide. As the refractile bodies dissolve, the pH of the solution may decrease, requiring the periodic addition of more base to maintain alkaline conditions. Refractile bodies have been completely solubilized at concentrations as high as 60 mg/ml or more. Moreover, solubilization has been achieved at urea concentrations as low as 1.0M. The solubilization conditions required (i.e., urea concentration, amount of urea solution used relative to the amount of refractile bodies and the solution pH) will depend on the particular refractile body composition and the amount of refractile bodies to be solubilized.

Although not critical to the present invention, one may employ a suitable non-interfering buffering agent to aid in dampening shifts in solution pH during the solubilization step. Suitable buffering agents include, but are not limited to, Tris(hyroxymethyl)aminomethane and ethanolamine. Tris(hydroxymethyl-)aminomethane, hereinafter referred to as "Tris", is preferred, since it is inexpensive and readily available. Tris concentrations between about 10 and 90 mM appear to not significantly affect somatotropin yield. A freshly prepared 50mM Tris solution has a pH of about 11.5. However, Tris, with a pK of 8.8 at 4° C., has only weak buffering capacity at this high pH. A Tris concentration between about 40 and 60 mM is preferred to minimize Tris usage while still maintaining some buffering capacity.

If the somatotropin is present in the refractile bodies in aggregated and/or oxidized form, it is preferred to have an exogenous reducing agent such as a β-mercaptoethanol or 1,4 dithiothreitol in the aqueous urea solution to promote cleavage of the intramolecular and intermolecular disulfide bonds. If such incorrectly folded monomer or aggregated somatotropin is present, the presence of reducing agent will typically enhance the recovery of biologically active somatotropin. It has been found that the reducing agent and the sulfhydral groups can oxidize concomitantly in the urea solution giving a good yield of correctly oxidized monomeric somatotropin and does not necessarily have to be removed prior to oxidation of the subject somatotropin. In the case of N-methionyl bovine somatotropin and N-methionyl porcine somatotropin expressed in an *E. coli* host cell it was found that the protein was sequested in the refractile bodies in substantially reduced form (no disulfide linkages). Hence, for these preparations the use of reducing reagents was unnecessary.

In another aspect of the present method, it has been further found that once solubilized, such somatotropins can be easily transformed to their native form. In thier native form, somatotropins contain two intramolecular disulfide bonds between four cysteine residues. Unfortunately, when undergoing oxidation from the reduced form the cysteine redidues may combine to form two intramolecular bonds in any one of three ways only one combination of which defines the native form. Likewise, cysteine redidues from one somatotropin molecule may form disulfide bonds with cysteine residues from another molecule producing dimers, trimers and higher oligomers. The ratio of correctly formed monomer to incorrectly formed monomer and oligomers is influenced by the conditions under which the somatotropin protein is folded and oxidized.

Prior to the present discovery, it was standard biochemical practice when naturing protein to exchange the protein from the denaturing solution (i.e., chaotropic solution) to an acceptable buffer solution such as sodium bicarbonate at a pH suitable for the particular protein in the presence of a reducing reagent, see Stryer, Biochemistry (2nd edition, 1981) pp 32-35, W. H. Freeman and Company and Bewley et al., "Human Pituitary Growth Hormone—The Reduction and Reoxidation of the Hormone", *Archives of Biochemistry and Biophysics,* 138, pp 338-346 (1970). The volume of buffer solution utilized was such that the protein concentrations was quite low, usually less than about 1.5 mg/ml. Oxidation of the protein was then accomplished by exposing the solution to air.

Formation of disulfide bonds in proteins is proposed to occur by a base catalyzed free radical mechanism such as that described by March in Adv. Organic Chemistry, McGraw Hill (1977). Being base catalyzed, the oxidation step is preferably carried out at alkaline pH. While the oxidation reaction forming the disulfide bonds will proceed at pH greater than about 7, an operating pH above the pK for a protein sulfhydral group (~8.4) is preferred. Specifically, an operating pH between about 9 and 12 is preferred. If a buffer is used, Tris(hydroxymethyl)amino methane is preferred.

Contrary to prior practice, it has now been found that somatotropins can be efficiently natured while still dissolved in the urea or dimethylsulfone solution by contacting the solution with a mild oxidizing agent such as hydrogen peroxide or air for a sufficient time to oxidize the sulfhydral groups forming intramolecular disulfide bonds. It has been further found that naturation can be carried out at somatotropin concentrations as high as 30 mg/ml or more, but preferably less than about 30 mg/ml and more preferably less than about 20 mg/ml. Naturation proceeds in an efficient manner in the presence of contaminating proteins of the host cell in the presence or absence of reducing reagents. The amount of somatotropin monomer may be determined by any suitable biochemical techniques such as radioimmunoassay (RIA), size exclusion chromatography and high performance liquid chromatography (HPLC).

In the absence of exogenous reducing agents such as β-mercaptoethanol and 1,4 dithiothreitol or precautions to exclude oxygen, oxidation of the somatotropin molecule begins upon solubilization. Urea concentration appears to be the most influential parameter affecting the yield of biologically active somatotropin monomer. Indeed, oxidation will occur at substantially any urea concentration at which the somatotropin will remain solubilized. It should be understood that once solubilized, somatotropins will remain in solution at reduced temperatures at urea concentrations of 1M or lower. Hence, to maximize production of such monomer one should adjust the urea concentration from that utilized in the solubilization step to that determined to be optimal for the renaturation step. The particular optimal concentration will necessarily depend on the particular somatotropin. When it is desirable to reduce the urea concentration following solubilization, dilution may be accomplished by addition of distilled water or buffer solution. One may choose to use reducing agent to temper the need for prompt action on adjustment of the urea concentration. In the absence of reducing agent, monomer yield decreases for MBS approximately 5 wt% for each hour lapsed prior to dilution of the urea concentration when 7.5M urea is used for solubilization.

In the case of N-methionyl bovine somatotropin, a urea concentration during naturation of between about 4M and 5M is preferred. Naturation appears optimal at about 4.5M with decreased monomer recovery and increased aggregate formation at both higher and lower urea concentrations. Accordingly, if 7.5M urea is used for solubilization, rapid dilution to 4.5M urea with distilled water or a suitable buffer such as Tris is preferred in the absence of reducing agent to mimimize oxidation at the higher non-optimal urea concentration.

In the case of N-methionyl porcine somatotropin, which differs from MBS in 18 amino acids, a urea concentration during reactivation of between 2.5M and 3.5M is preferred. Naturation appears optimal at about 3M urea with decreased monomer recovery and increased aggregate formation at both higher and lower urea concentrations. Likewise, rapid dilution from 7.5M to 3M urea with good mixing, a suitable buffer such as Tris is preferred in the absence of reducing agent to minimize renaturation at higher non-optimal urea concentrations.

Somatotropins solubilized and natured in the above-described manner were subsequently purified by standard chromatographic techniques. Bioactivity was indicated by positive response to rat growth bioassay tests. In this assay, the bioactivity of the heterologous somatotropin is assessed relative to a known lot of somatotropin material (e.g., bovine or porcine pituitary somatotropin) by relating the amount of weight gain demonstrated by hypophysectomized rats to varying amounts of administered material. Regression slopes of body weight gain versus dosages administered for the particular somatotropin material are compared to the known standard (i.e., pituitary material) and a relative bioactivity in U(units)/mg growth hormone calculated for the heterologous somatotropin material.

N-methionyl bovine somatotropin solubilized and natured in the method embraced by the present invention and subsequently purified was subsequently administered to dairy cows. Dairy cows administered such a preparation produced 10% to 40% (by weight) more milk than control animals, see Eppard et al. "The Effect of Long-term Administration of Growth Hormone on Performance of Lactating Dairy Cows", Proceedings of the 1984 Cornell Nutrition Conference.

The following examples are included to better elucidate the practice of the present invention. It should be understood that these examples are included for illustrative purpose only and are not, in any way, intended to limit the scope of the present invention.

EXAMPLE 1

The present invention has been demonstrated by the solubilization of N-methionyl bovine somatotropin (MBS) expressed in *E. coli* as generally described in Seeburg et al., *DNA* 2(1): 37–45 (1983). Details for the individual steps can be found in Goeddel et al., *Nature* Vol 281 (October, 1979); DeBoert et al., *Promoters: Structure and Function,* pp 462–481 Praeger Scientific Publishing Co., (1982); and Miozzari et al., *J. Bacteriology* Vol 133, pp 1457–1466 (1978). Harvested cells were disrupted by double passage through a Manton Gaulin homogenizer. Refractile bodies, containing MBS, were pelleted from the homogenate solution under low speed centrifugation. The supernatant was discarded, refractile bodies resuspended, washed and again pelleted. The supernatant was again discarded leaving a substantially pure refractile body preparation.

Refractile bodies prepared in the manner described above were subjected to various concentrations of an aqueous urea solution at various pH levels at 25° C. All buffered solutions contained 100 mM Tris-base. pH adjustment was accomplished by addition of HCl. The final refractile body concentration was about 4 mg/ml of solution. The extent of dissolution was determined spectrophotometrically assuming the refractile bodies were totally proteinaceous and using an extinction coefficient ($\epsilon$) of 0.68 at 277 nm and 1 cm. path length, as indicative of a protein concentration of 1 mg/ml. The starting concentration was determined spectrophotometrically for a completely dissolved sample. The results of the above described experiment are illustrated in FIG. 1. This data supports the unexpected discovery that adjustments of the pH to alkaline conditions substantially enhances the degree of solubilization.

EXAMPLE 2

Figure 2:
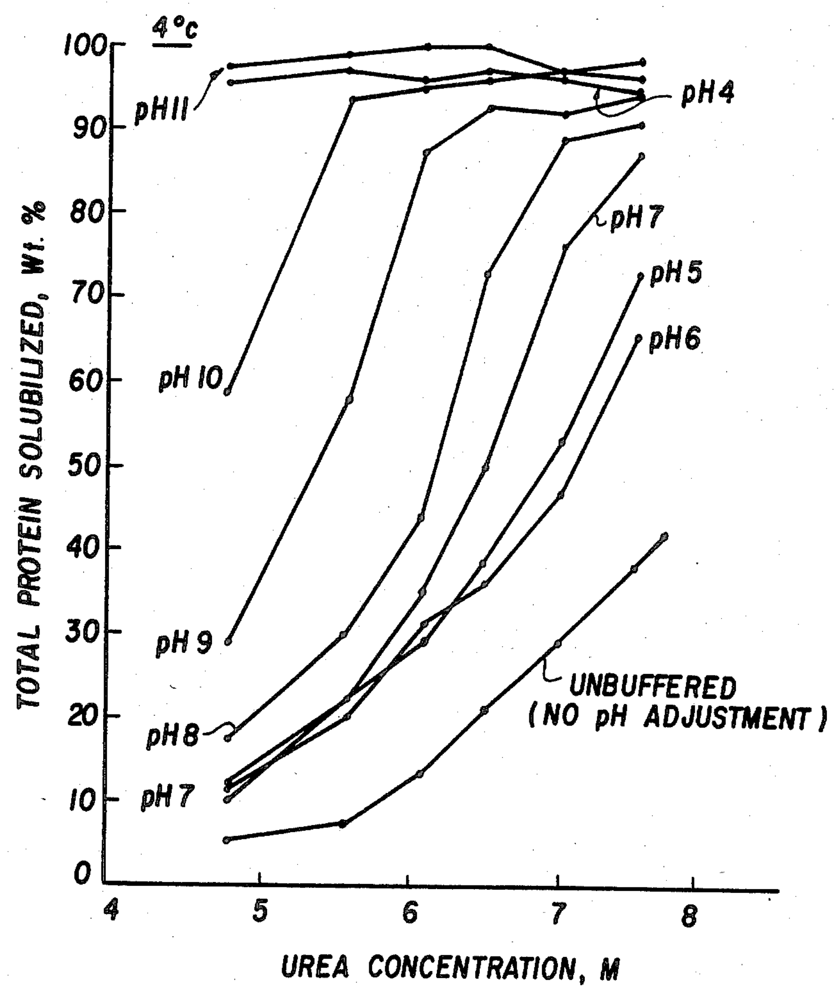

The procedure described in Example 1 was followed except that the temperature was maintained at 4° C. and the pH was adjusted to both acidic and alkaline levels. As on Example 1, all buffered solutions contained 100 mM Tris-base. pH adjustment to acidic levels was accomplished by addition of acetic acid. The results of this experiment are illustrated in FIG. 2. Comparing FIGS. 1 and 2 at constant urea concentration and a given pH will show the solubilization enhancement obtained at reduced temperatures (4° C.) compared to that at room temperatures (25° C.).

COMPARATIVE EXAMPLE A

Refractile bodies containing MBS were prepared in the manner described in Example 1. Refractile bodies were admixed with a 10M urea solution without pH adjustment such that the final refractile body concentration was about 5.0 mg/ml. The solution was mixed and allowed to equilibrate overnight at 4° C. The degree of solubilization was determined to be only about 2.9 mg/ml by the spectrophotometric method described above. The starting concentration of refractile bodies was determined by adding enough urea solution to completely dissolve the refractile bodies spectrophotometrically measuring the completely dissolved solution and adjusting for dilution.

COMPARATIVE EXAMPLE B

Refractile bodies containing MBS, prepared in the manner described in Example 1, were admixed with an aqueous 8.0M urea solution without pH adjustment such that the final refractile body concentration was about 5.0 mg/ml. The solution was mixed and allowed to equilibrate overnight at 4° C. The degree of solubilization was determined to be about 2.4 mg/ml by the spectrophotometric method described above. The starting concentration of refractile bodies was determined by adding enough urea solution to completely dissolve the refractile bodies spectrophotometrically measuring the completely dissolved solution and adjusting for dilution.

EXAMPLE 3

Refractile bodies containing MBS, prepared in the manner described in Example 1, were admixed with an unbuffered aqueous 4.5M urea solution such that the refractile body concentration was about 66 mg/ml. The solution pH was adjusted from pH 7 to pH 11 with dilute NAOH. The solution clarified indicating complete solubilization. The refractile body concentration was determined to be 66 mg/ml by spectrophotometric analysis described in Example 1.

EXAMPLE 4

Figure 3:
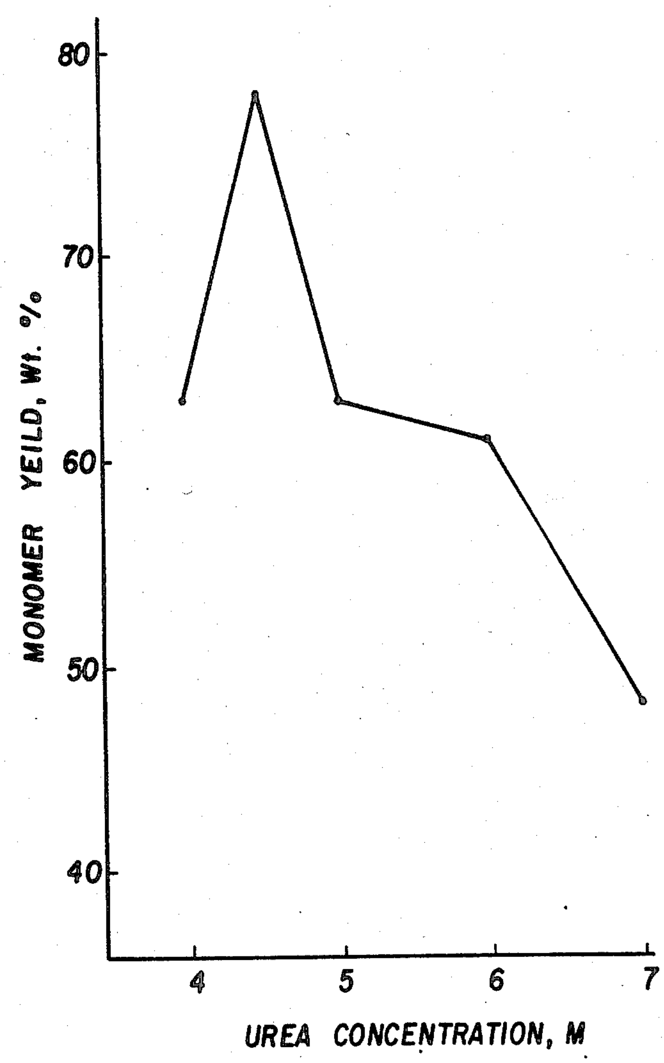

Refractile bodies containing MBS, prepared in the manner described in Example 1, were solubilized in an aqueous 7.5M urea solution containing 100 mM TRIS at pH 10.5. The urea concentration was adjusted to various levels by adding 100 mM TRIS and the total protein concentration maintained at about 1 mg/ml (determined by spectrophotometric analysis of a completely dissolved sample) by addition of a volume of the appropriate urea solution. The dissolved MBS was permitted to oxidize by exposing the solution to air under stirred conditions for a twenty-four hour period. The results are graphically illustrated in FIG. 3. MBS monomer yield is indicated as a weight percent of total MBS content. As shown in FIG. 3, optimal naturation efficiency is obtained at a urea concentration of about 4.5M.

EXAMPLE 5

Following the procedure described in Example 4, refractile bodies containing MBS were solubilized in an aqueous 7.5M urea solution having 100 mM TRIS at pH 10.5. Following solubilization, the solution was diluted to 4.5M urea with 100 mM Tris and the pH adjusted to levels between 10.5 and 8.5. These individual trials were permitted to oxidize by exposure to air under stirred conditions for 24 hours. MBS monomer and oligomer content was determined by HPLC. While the results indicate a relatively flat response in naturation efficiency versus solution pH during oxidation, there is a trend toward higher efficiency at higher pH. In addition, the base catalyzed oxidation proceeds faster at the more alkaline pH.

EXAMPLE 6

Approximately 150 ml of a refractile body preparation, prepared in the manner described in Example 1, was added to about 850 ml of an aqueous 5.3M urea solution at 4° C. The resulting 4.5M urea solution was adjusted to pH 11 with 50 wt % NaOH solution. The refractile bodies completely dissolved resulting in a total MBS concentration of about 12.4 mg/ml. The solution was stirred at 4° C. overnight to oxidize the MBS. HPLC analysis of the oxidized solution indicated an MBS monomer yield efficiency of about 80 wt%.

EXAMPLE 7

N-methionyl porcine somatotropin (MPS) was expressed in *E. coli* using the general teachings of the references listed in Example 1. Following recovery of the refractile bodies containing the MPS using the method previously described, they were solubilized at 4° C. in 7.5M urea, 90 mM Tris pH 11.0. One hundred thirteen mg of refractile body pellet (wet wt.) were dissolved per milliliter of the above urea solution. Samples were diluted with 90 mM Tris and/or urea to obtain urea concentrations of 4.5M, 3.0M and 2.0M with an MPS concentration of 4 mg/ml based on the wet weight of the refractile body pellet. The samples were permitted to oxidize by exposure to air overnight under stirred conditions. Assay by HPLC indicated an optimal MPS monomer yield at a urea concentration of 3M.

EXAMPLE 8

Following the procedure outlined in Example 7, MPS was solubilized at 4° C. in aqueous 7.5M urea, 90 mM Tris at pH 11 at three different concentrations (20, 40 and 80 mg pellet (wet wt.) per ml of the above urea solution). Samples of the solutions were diluted with 90 mM Tris and/or urea to obtain a urea concentration of 3M and MPS concentrations of 1mg/ml. Diluted MPS solutions were exposed to air under stirred conditions at 4° C. for 56 hours. Assay by HPLC indicated an average MPS monomer yield of 69 wt%.

EXAMPLE 9

The procedure of Example 8 was followed except solubilization and naturation was performed in the presence of 0.1 mM 1,4-dithiothreitol. Assay by HPLC indicated an average MPS monomer yield of 66 wt%.

EXAMPLE 10

Three variants of BGH, namely $Ala_{-1}$, $Ala_{-1}V_{126}$ and $Met_{-1}Val_{126}$, were expressed in *E. coli* following the procedures described in commonly commonly assigned U.S. patent application Ser. No. 704,362 filed Feb. 22, 1985 by G. G. Krivi entitled "Production of Proteins in Procaryotes", specifically incorporated herein by reference. The BGH variants were solubilized and natured following the general procedures described in Example 1.

Refractile bodies containing the respective BGH varient were recovered as described in Example 1. Approximately 300 grams (wet wt.) of refractile bodies were suspended in water to yield a 1 liter slurry. This slurry was added to about 5 liters of 9M urea, 108 mM Tris resulting in a solubilization solution comprising the respective BGH variant in 7.5M urea and 90 mM Tris at pH 10.5 and 4° C. Complete solubilization occurred after stirring for a few minutes. Four liters of cold water were slowly added to yield a naturation solution comprising the respective BGH variant in 4.5M urea, 54 mM Tris at pH 10.5 and 4° C. The solution was stirred and the respective BGH variant permitted to oxidize by exposing the solution to air for about 48 hours. The oxidized BGH variant solutions were assayed by HPLC indicating a monomer yield of about 60–70 wt% for all three BGH variants.

EXAMPLE 11

The structural homology of somatotropin protein obtained as described above to that of the natural pituitary somatotropin was determined by circular dichroism as described by Bewley, *Recent Progress in Hormone Research,* Vol. 35 pp 155–210, Academic Press. Specifically, MBS and the $Ala_{-1}$ variant of BGH was compared to bovine pituitary somatotropin. Samples were dissolved in a 50 mM sodium bicarbonate, pH 9.5, and analyzed by the above-described technique. The results of this analysis confirm that the recombinant somatotropin prepared in the manner described herein was in its native conformation following naturation.

EXAMPLE 12

Refractile bodies containing MBS, prepared in the manner described in Example 1, were admixed with an unbuffered aqueous 1.0M urea solution at 4° C. The pH was adjusted and maintained at 12.1 with sodium hydroxide. The solution clarified indicating complete solubilization. The refractile body concentration was determined to be about 10 mg/ml by spectrophotometric analysis as described in Example 1.

EXAMPLE 13

Figure 4:
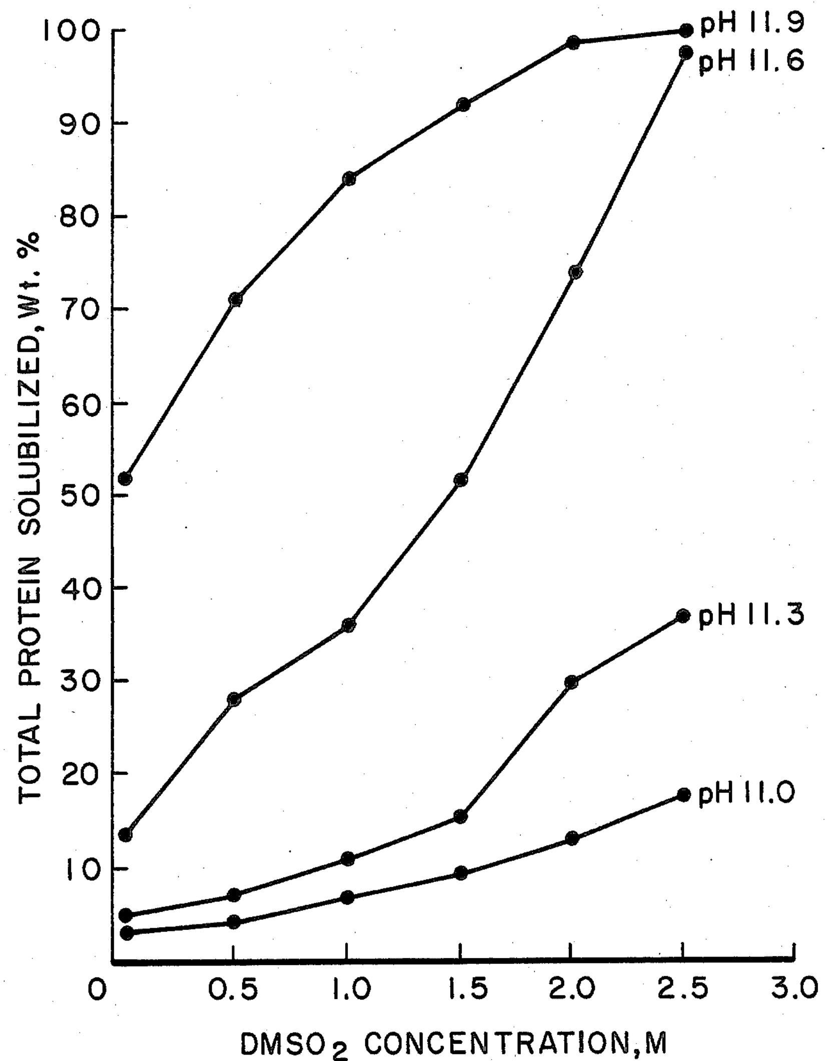
Figure 5:
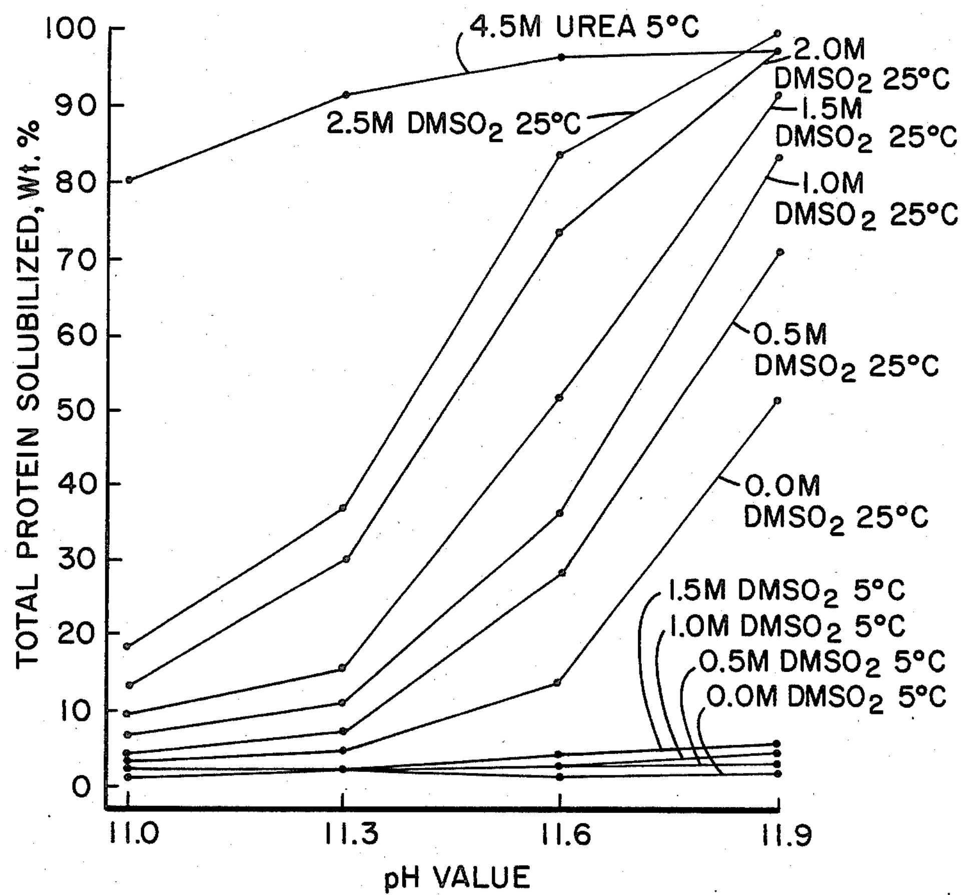

Refractile bodies containing MBS were prepared in the manner described in Example 1. The refractile bodies were dissolved in solutions of dimethylsulfone at concentrations of 0.5, 1.0, 1.5, 2.0 and 2.5M, at pH values 11.0, 11.3, 11.6 and 11.9 (unbuffered, NaOH addition) and at temperatures of 5° C. and 25° C. Control solutions contained no solvent other than water for each pH value. The concentration of refractile body slurry in each of the dimethylsulfone solutions was 15% v/v at the beginning of solubilization. Dissolution of refractile bodies was determined by UV absorbance at 277 nm. Maximum dissolution was determined from measuring the UV absorbance of a refractile body control solution in 4.5M urea at pH 11.9 and 5° C. Solubilization of refractile bodies in the dimethylsulfone test solutions was measured and expressed as a percentage of the absorbance of the refractile body control solution. Measurements were taken at one hour after addition of the sodium hydroxide. FIG. 4 is a graph of percent solubilization as a function of $DMSO_2$ molarity at four different pH levels and at 25° C. FIG. 5 is a graph of percent solubilization as a function of pH at different $DMSO_2$ molarities at 25° C.

EXAMPLE 14

Refractile bodies containing MBS were prepared in the manner described in Example 1. The refractile bodies were dissolved in solutions of urea (2.25M; 4.5M), and also in solutions of dimethylsulfone (0.5, 1.0, 1.5, 2.0 and 2.5M), and also in a urea-dimethylfulone mixture (2.25M urea + 1.45M $DMSO_2$). The pH values for each of these test solutions were adjusted and maintained at 11.0, 11.3, 11.6 and 11.9 (unbuffered, NaOH addition) at a temperature of 5° C. Control solutions contained no solvent other than water for each pH value. The concentration of refractile body slurry in each of the solutions was 15% v/v at the beginning of solubilization. Dissolution of refractile bodies was determined as in Example 13. Measurements were taken at one hour after addition of the sodium hydroxide. It was observed that solubilization in urea at 2.5M was about as effective as solubilization in a mixture of urea (@ 2.25M) and dimethylsulfone (@ 1.45M).

What is claimed is:

1. A method for naturation of somatotropin protein which comprises contacting a dimethylsulfone or urea-dimethylsulfone solution containing said protein with a mild oxidizing agent for a time sufficient to form intramolecular disulfide bonds between cysteine residues contained in said somatotropin protein.

2. The method of claim 1 in which the somatotropin protein is natured in an aqueous dimethylsulfone solution.

3. The method of claim 2 in which the naturation is conducted in a dimethylsulfone concentration between about 0.5 and 2.4M.

4. The method of claim 3 in which the naturation is conducted at a pH above 9.

5. The method of claim 3 in which the naturation is conducted at a pH between about 9 and 12.

6. The method of claim 3 in which the naturation is conducted at a temperature above the freezing point of the solution and below about 30° C.

7. The method of claim 1 in which the somatotropin is bovine somatotropin.

8. The method of claim 1 in which the naturation is conducted at a dimethylsulfone concentration between about 0.5 and 2.4M; a temperature above the freezing point of the solution and below about 30° C.; and a pH between about 9 and about 12.

9. The method of claim 1 wherein the protein has been initially solubilized from refractile bodies of a host cell containing said protein by contacting said bodies with an effective amount and concentration of a weak denaturant at a pH effective to solubilize said protein.

10. The method of claim 9 in which the weak denaturant is selected from the group consisting of urea, dimethylsulfone and urea-dimethylsulfone.

11. The method of claim 10 in which the solubilization is conducted at a temperature above the freezing point of the solution and below about 25° C.

12. The method of claim 10 in which solubilization is conducted at a pH above about 9.

13. The method of claim 10 in which solubilization is conducted at a pH between about 9 and about 12.

14. The method of claim 10 in which solubilization is conducted at a pH between about 9 and about 12 and a temperature of about 4° C.

15. The method of claim 10 in which the host cell is a strain of the bacterial species *Escherichia coli.*

16. The method of claim 10 in which the somatotropin is bovine somatotropin.

17. The method of claim 10 in which the host cell is a strain of the bacterial species *Escherichia coli.*

18. The method of claim 17 in which said solution comprises urea and the urea concentration is between about 1.0M and 10M; the pH is maintained between about 9 and about 12; and the temperature is maintained above the freezing point of the solution and below about 25° C.

19. The method of claim 17 in which said solution comprises dimethylsulfone and the dimethylsulfone concentration is between about 0.5M and about 2.4M; the pH is maintained between about 11.25 and about 12; and the temperature is maintained between about 5° C. and about 30° C.

* * * * *

UNITED STATES PATENT AND TRADEMARK OFFICE

CERTIFICATE OF CORRECTION

PATENT NO. : 4,694,073

DATED : September 15, 1987

INVENTOR(S) : Larry A. Bentle et al.

It is certified that error appears in the above-identified patent and that said Letters Patent is hereby corrected as shown below:

Title of Invention should read -- METHOD OF SOMATOTROPIN SOLUBILIZATION AND NATURATION USING DIMETHYLSULFONE --.

Table I, under lines 121-140, the abbreviations were left off on the table. They should appear as follows:

-- BGH
PGH
OGH
AGH
HGH --.

Table II, column 5, across from Threonine and under Ovine it is shown as "2" and should read -- 12 --.

Signed and Sealed this

Twenty-sixth Day of April, 1988

*Attest:*

DONALD J. QUIGG

*Attesting Officer*

*Commissioner of Patents and Trademarks*